US012653508B2

(12) United States Patent
Chono et al.

(10) Patent No.: US 12,653,508 B2
(45) Date of Patent: Jun. 16, 2026

(54) ULTRASOUND TIME SERIES DATA PROCESSING APPARATUS AND ULTRASOUND TIME SERIES DATA PROCESSING PROGRAM

(71) Applicant: FUJIFILM Healthcare Corporation, Kashiwa (JP)

(72) Inventors: Tomoaki Chono, Chiba (JP); Eiji Kasahara, Chiba (JP); Katsunori Asafusa, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 106 days.

(21) Appl. No.: 18/200,743

(22) Filed: May 23, 2023

(65) Prior Publication Data

US 2023/0397905 A1 Dec. 14, 2023

(30) Foreign Application Priority Data

Jun. 9, 2022 (JP) ................................. 2022-093657

(51) Int. Cl.
*A61B 8/00* (2006.01)

(52) U.S. Cl.
CPC ............ *A61B 8/5223* (2013.01); *A61B 8/488* (2013.01); *A61B 8/485* (2013.01)

(58) Field of Classification Search
CPC ....... A61B 8/5223; A61B 8/488; A61B 8/485; A61B 8/5207
See application file for complete search history.

(56) References Cited

U.S. PATENT DOCUMENTS 9,589,374 B1 3/2017 Gao et al.
2005/0251013 A1 11/2005 Krishnan et al.
(Continued)

FOREIGN PATENT DOCUMENTS

CN 111345847 A 6/2020
JP H01-181852 A 1/1989
(Continued)

OTHER PUBLICATIONS

Japanese official action (and English translation thereof) dated Aug. 5, 2025 in connection with Japanese Patent Application No. 2022-093657.

(Continued)

*Primary Examiner* — Keith M Raymond
*Assistant Examiner* — Johnathan Maynard
(74) *Attorney, Agent, or Firm* — Paul Teng

(57) ABSTRACT

By repeatedly performing ultrasound transmission and reception with respect to a single scan plane designated within a target subject's body, a temporally sequential target set of time series data is obtained in a reception unit, an image generation unit, a tracking processing unit, an elastography processing unit, or a Doppler processing unit. A feature prediction unit inputs the target set of time series data into a learner, and predicts a feature indicated by the target set of time series data based on output data output from the learner in response to the target set of time series data, wherein the learner is trained to predict and output, based on an input set of time series data, a feature indicated by that set of time series data. A display control unit notifies a result of prediction by the feature prediction unit to a user.

15 Claims, 6 Drawing Sheets

(56)        References Cited

U.S. PATENT DOCUMENTS

| | | | |
|---|---|---|---|
| 2013/0158399 A1* | 6/2013 | Chono | A61B 8/5284 |
| | | | 600/437 |
| 2014/0369564 A1* | 12/2014 | Chono | A61B 6/469 |
| | | | 382/103 |
| 2019/0343490 A1* | 11/2019 | White | A61B 8/5292 |
| 2020/0043602 A1* | 2/2020 | Kim | G06N 3/02 |
| 2020/0060657 A1* | 2/2020 | Aladahalli | G16H 50/30 |
| 2020/0107818 A1* | 4/2020 | Keshet | A61B 8/0883 |
| 2020/0185084 A1* | 6/2020 | Syeda-Mahmood | |
| | | | G06V 10/7515 |
| 2020/0297318 A1 | 9/2020 | Srinivasa Naidu et al. | |
| 2020/0334818 A1 | 10/2020 | Igarashi et al. | |
| 2021/0137416 A1* | 5/2021 | Canfield | G16H 50/30 |
| 2021/0192738 A1 | 6/2021 | Meguro | |
| 2021/0259664 A1* | 8/2021 | Hare, II | A61B 8/469 |
| 2022/0395251 A1* | 12/2022 | Tsymbalenko | A61B 8/085 |
| 2023/0058450 A1* | 2/2023 | Lee | G16H 30/20 |
| 2023/0368376 A1 | 11/2023 | Kasahara et al. | |
| 2023/0368917 A1 | 11/2023 | Kasahara et al. | |

FOREIGN PATENT DOCUMENTS

| | | |
|---|---|---|
| JP | 2002-209889 A | 7/2002 |
| JP | 2007-530160 A | 11/2007 |
| JP | WO2012/029816 A1 | 10/2013 |
| JP | 2017-012607 A | 1/2017 |
| JP | 2020-049212 A | 4/2020 |
| JP | 2020-081460 A | 6/2020 |
| JP | 2020-146455 A | 9/2020 |
| JP | 2021-501656 A | 1/2021 |
| JP | 2021-100555 A | 7/2021 |
| JP | 2021-122705 A | 8/2021 |
| JP | 2023-168940 A | 11/2023 |
| JP | 2023-168941 A | 11/2023 |
| WO | WO2018-180386 A1 | 10/2018 |

OTHER PUBLICATIONS

Japanese official action (and English translation thereof) dated Nov. 11, 2025 in Connection with counterpart Japanese Patent Application No. 2022-093657.

Apr. 2, 2026 Chinese official action (and machine translation on English thereof) in connection with Chinese Patent Application No. 2023105945232.

* cited by examiner

TIME

θ

F

F

F

ULTRASOUND TIME SERIES DATA PROCESSING APPARATUS AND ULTRASOUND TIME SERIES DATA PROCESSING PROGRAM

CROSS REFERENCE TO RELATED APPLICATION

This application claims priority to Japanese Patent Application No. 2022-093657 filed on Jun. 9, 2022, which is incorporated herein by reference in its entirety including the specification, claims, drawings, and abstract.

TECHNICAL FIELD

The present specification discloses an ultrasound time series data processing apparatus and an ultrasound time series data processing program.

BACKGROUND

Conventionally, ultrasonic diagnosis apparatuses have been used to perform transmission and reception of ultrasound with respect to a subject's body and to generate an ultrasound image based on a set of frame data (i.e., a plurality of ultrasound beam data items corresponding to one ultrasound image) obtained thereby. Conventionally, there have been proposed techniques for automatically determining a disease shown in an ultrasound image.

WO 2018/180386 A discloses an ultrasound image diagnosis assisting method in which, using ultrasound images (still images) showing tumors as diseases and other ultrasound images (still images) as training data, a model is trained to distinguish tumors in input ultrasound images, and by inputting a determination target ultrasound image into the trained model, a tumor is distinguished in the determination target ultrasound image. In particular, in the ultrasound image diagnosis assisting method disclosed in WO 2018/180386 A, based on a finding that speckle noise or the like is generated sporadically, a tumor candidate region that occurs at identical positions in consecutive frames, which are ultrasound images temporally continuous with the determination target ultrasound image, is handled as a definitive tumor region.

For example, as in WO 2018/180386 A, by inputting an ultrasound image into a trained model (or learner), it is possible to predict a feature shown in the ultrasound image. However, there is room for improvement in prediction of a feature in an ultrasound image using a learner. For example, if a learner can predict a feature in an ultrasound image by considering movement or the like of a subject's body shown in a time series sequence of ultrasound images (that is, a moving image), prediction accuracy is expected to be improved.

An ultrasound time series data processing apparatus disclosed in the present specification is directed to improving accuracy of prediction of a feature shown in an ultrasound image.

SUMMARY

An ultrasound time series data processing apparatus disclosed in the present specification includes a feature prediction unit configured to input, into a feature prediction learner, a target set of time series data which is a set of time series data generated by repeatedly performing a plurality of cycles of ultrasound transmission and reception with respect to a single scan plane designated within a target subject's body, and to predict a feature regarding the target set of time series data based on an output from the feature prediction learner in response to said input. The feature prediction learner is trained using, as training data, a combination of a training set of time series data and information indicating a feature regarding the training set of time series data. The training set of time series data is a set of time series data indicating a change in signal over time, and is generated by repeatedly performing a plurality of cycles of ultrasound transmission and reception with respect to a single scan plane designated within a subject's body. The feature prediction learner is trained to predict and output, based on an input set of time series data, a feature regarding that set of time series data. The ultrasound time series data processing apparatus further includes a notification unit configured to notify a result of prediction by the feature prediction unit to a user.

The above-noted feature may be at least one of: a type of examination to be performed using a set of time series data; a type of tissue cross section shown by the set of time series data; a measurement position that should be designated; a disease indicated by the set of time series data; or a type of artifact generated in the set of time series data.

Further, the above-noted set of time series data may be at least one of: a time series sequence of ultrasound images; a time series sequence of frame data, which are data before imaging; trajectory information showing a trajectory of a speckle; time series elastography information indicating a change in amount of deformation over time of a body portion under examination; and time series Doppler signals indicating a change in velocity over time of a body portion under examination or blood.

According to the above-described configuration, the feature prediction learner is trained using a temporally sequential training set of time series data, so that the feature prediction learner is capable of outputting a feature of a set of time series data in consideration of a change in signal over time in the set of time series data. By inputting a temporally sequential target set of time series data into the feature prediction learner trained as such, a feature of an ultrasound image can be predicted more accurately, at least as compared to a case where the feature of the ultrasound image is predicted by inputting the ultrasound image into a learner trained using ultrasound images that are still images.

The feature prediction unit may input the target set of time series data into the feature prediction learner which is selected based on a user instruction from among a plurality of feature prediction learners trained to predict and output features different from each other.

According to the above-described configuration, the user can obtain a result of prediction of a desired feature regarding the target set of time series data.

The feature prediction unit may input the target set of time series data into a plurality of feature prediction learners trained to predict and output features different from each other, and predicts the feature regarding the target set of time series data based on a combination of outputs from the plurality of feature prediction learners.

According to the above-described configuration, accuracy of prediction of the feature regarding the target set of time series data is expected to be further improved. For example, the feature prediction unit predicts the type of examination that should be performed using the target set of time series data based on an output from the feature prediction learner configured to predict a type of examination to be performed using a set of time series data, and identifies a plurality of diseases that can be determined based on the predicted type of examination. After that, by inputting the target set of time series data into the feature prediction learner configured to predict a disease indicated by a set of time series data, the feature prediction unit predicts the disease indicated by the target set of time series data in a manner of selecting from among the plurality of diseases identified earlier. With this arrangement, accuracy of disease prediction is expected to be further improved.

The target set of time series data and the training set of time series data may be sets of time series data that correspond to the same period of a pulsation cycle of a subject.

According to the above-described configuration, since the period of the target set of time series data and the period of the training set of time series data are the same period of a pulsation cycle, accuracy of output from the feature prediction learner is improved, and as a result, accuracy of prediction of the feature indicated by the target set of time series data can be further improved.

The ultrasound time series data processing apparatus may further includes a time series data generation unit configured to generate the target set of time series data.

According to the above-described configuration, the feature regarding the target set of time series data can be predicted in an ultrasonic diagnosis apparatus configured to perform ultrasound transmission and reception with respect to a subject's body and to generate the target set of time series data.

The feature prediction unit may repeatedly execute prediction of the feature regarding the target set of time series data obtained by referring to a current point of time as a reference point.

According to the above-described configuration, the user can obtain a result of prediction of the feature regarding the most recent target set of time series data.

Based on an electrocardiac waveform obtained from the target subject, the feature prediction unit may execute prediction of the feature regarding the target set of time series data obtained by referring, as a reference point, to a point of time at which the target subject's heartbeat intervals have become stable.

According to the above-described configuration, it is possible to perform prediction of the feature in a target set of time series data obtained in a state in which the heartbeat intervals are stable.

The feature prediction unit may execute prediction of the feature regarding the target set of time series data obtained by referring, as a reference point, to a point of time at which a user has operated an ultrasound probe configured to perform ultrasound transmission and reception.

According to the above-described configuration, the user can obtain a prediction of the feature regarding the target set of time series data each time the user operates the ultrasound probe.

An ultrasound time series data processing program disclosed in the present specification is configured to cause a computer to function as: a feature prediction unit configured to input, into a feature prediction learner, a target set of time series data which are a set of time series data generated by repeatedly performing a plurality of cycles of ultrasound transmission and reception with respect to a single scan plane designated within a target subject's body, and to predict a feature regarding the target set of time series data based on an output from the feature prediction learner in response to said input, wherein the feature prediction learner is trained using, as training data, a combination of a training set of time series data and information indicating a feature regarding the training set of time series data, the training set of time series data being a set of time series data indicating a change in signal over time and being generated by repeatedly performing a plurality of times of ultrasound transmission and reception with respect to a single scan plane designated within a subject's body, and wherein the feature prediction learner is trained to predict and output, based on an input set of time series data, a feature regarding that set of time series data; and a notification unit configured to notify a result of prediction by the feature prediction unit to a user.

According to the ultrasound time series data processing apparatus disclosed in the present specification, accuracy of prediction of a feature shown in an ultrasound image can be improved.

BRIEF DESCRIPTION OF DRAWINGS

Embodiment(s) of the present disclosure will be described based on the following figures, wherein.

DESCRIPTION OF EMBODIMENTS

Figure 1:
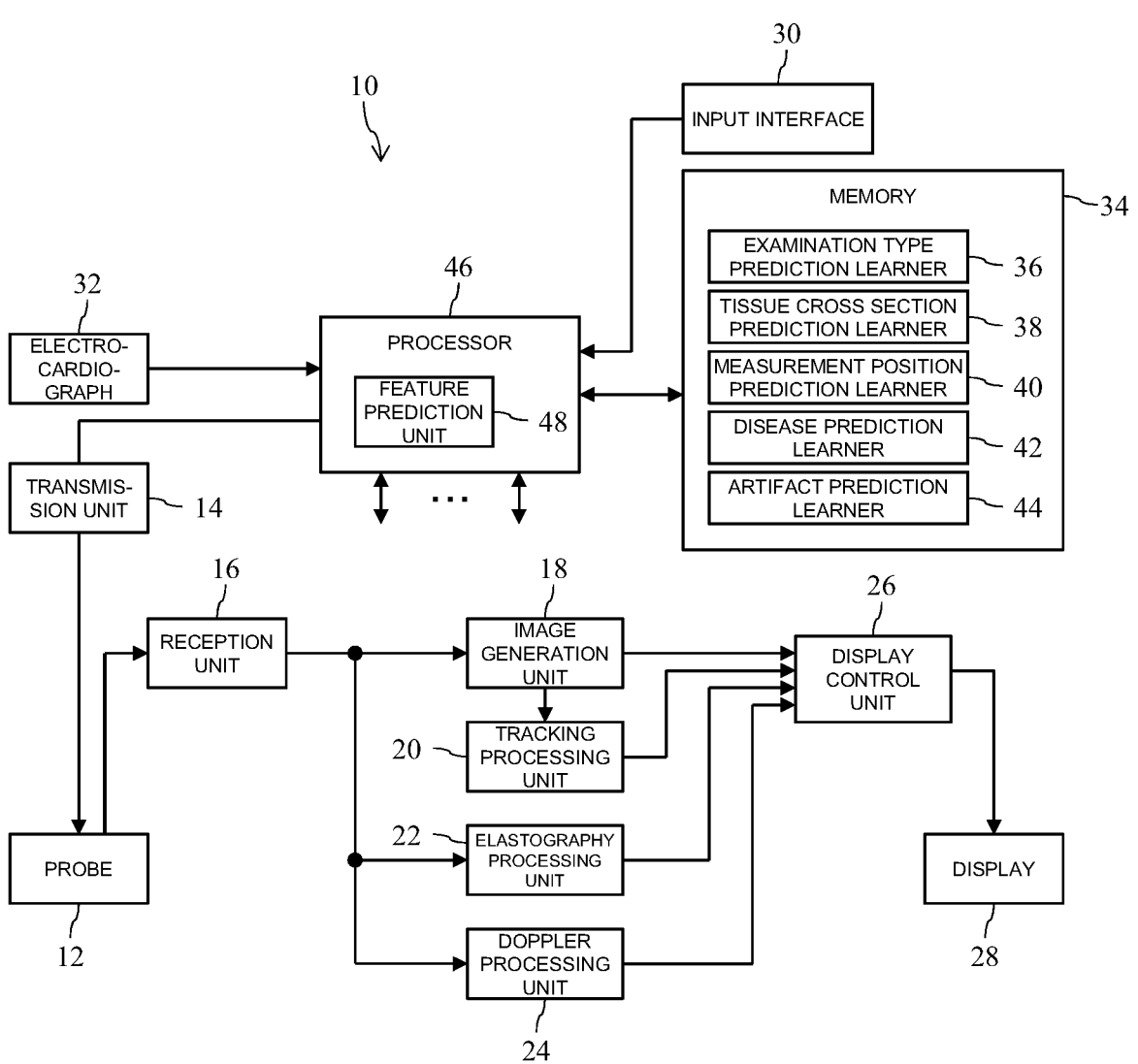
FIG. 1 is a block diagram of an ultrasonic diagnosis apparatus according to an embodiment.

FIG. 1 is a block diagram of an ultrasonic diagnosis apparatus 10, which is an ultrasound time series data processing apparatus according to an embodiment. The ultrasonic diagnosis apparatus 10 is a medical apparatus installed in a medical institution such as a hospital and used in ultrasonic examination.

As will be described in detail later, the ultrasonic diagnosis apparatus 10 is an apparatus that scans an ultrasound beam over a subject's body and generates ultrasound images based on frame data obtained thereby. More specifically, the ultrasonic diagnosis apparatus 10 generates, based on the frame data, tomographic images (or B-mode images) obtained by converting amplitude strength of waves reflected from a scan plane into brightness.

The ultrasonic diagnosis apparatus 10 has a speckle tracking function of tracking small dots (or speckles) in the time direction in a plurality of B-mode images arranged in time series. The speckle tracking function is used, for example, when evaluating movement (i.e., contraction and relaxation) of a predetermined portion of the cardiac muscle. The ultrasonic diagnosis apparatus 10 further has an elastography function, which involves applying pressure to a body portion under examination by a method such as pressing a probe 12 against a subject's body surface, estimating an amount of deformation of the body portion under examination caused in response to the pressure, and displaying the amount of deformation of the body portion under examination in color in a superimposed manner on a B-mode image. The ultrasonic diagnosis apparatus 10 additionally has a color flow mapping function (or color Doppler function), which involves calculating a movement velocity of a tissue inside a subject's body based on a difference between frequencies of transmitted waves and reflected waves, and displaying the movement velocity in color in a superimposed manner on a B-mode image.

The probe 12, which is an ultrasound probe, is a device for performing transmission of ultrasound waves and reception of reflected waves. Specifically, the probe 12 is abutted on a subject's body surface, transmits ultrasound waves toward the subject's body, and receives reflected waves reflected by tissues inside the subject's body. Inside the probe 12, there is provided a transducer array composed of a plurality of transducers. Each transducer included in the transducer array is supplied with a transmission signal which is an electric signal from a transmission unit 14 described later, and an ultrasound beam (or transmission beam) is thereby generated. Further, each transducer included in the transducer array receives a reflected wave from a subject's body, converts the reflected wave into a reception signal which is an electric signal, and transmits the reception signal to a reception unit 16 described later.

At the time of ultrasound transmission, in response to control by a processor 46 described later, the transmission unit 14 supplies a plurality of transmission signals in parallel to the probe 12 (more specifically, to the transducer array). As a result, ultrasound waves are transmitted from the transducer array. The transmission unit 14 supplies the transmission signals such that a transmission beam transmitted from the probe 12 is electronically scanned in a scan plane.

At the time of reception of reflected waves, the reception unit 16 receives a plurality of reception signals in parallel from the probe 12 (more specifically, from the transducer array). In the reception unit 16, the reception signals are subjected to phase alignment and summation (or delay and summing), and reception beam data are thereby generated.

Figure 2:
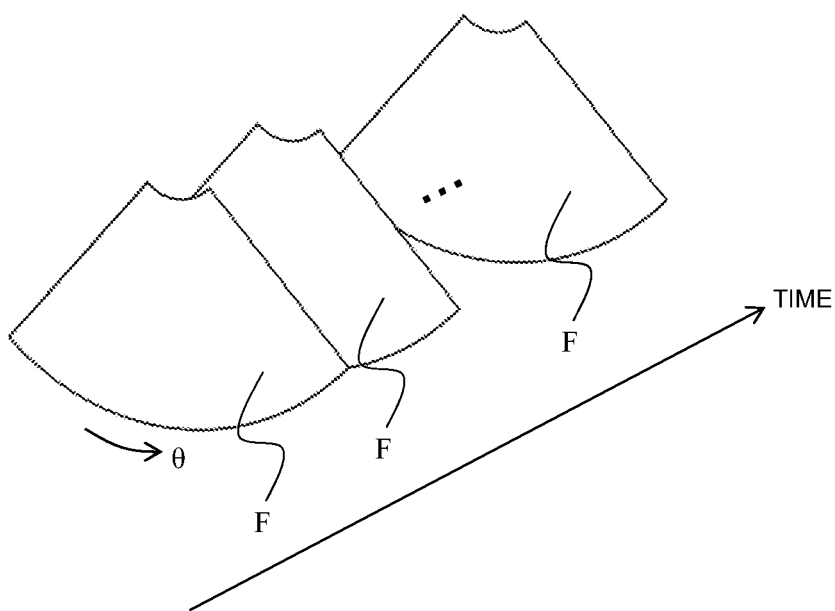
FIG. 2 is a conceptual diagram showing a time series sequence of frame data.

FIG. 2 is a conceptual diagram showing a time series sequence of frame data. An ultrasound beam from the probe 12 is scanned in a scan plane in a θ direction, and one set of frame data F is generated, which is composed of a plurality of reception beam data arrays and which corresponds to one ultrasound image. Scanning of an ultrasound beam with respect to a single scan plane designated within a subject's body is repeated a plurality of times. As a result, temporally sequential sets of frame data F (that is, a sequence of frame data) are generated.

The generated sets of frame data F are transmitted to an image generation unit 18, an elastography processing unit 22, or a Doppler processing unit 24.

Referring again to FIG. 1, the image generation unit 18 is composed of a digital scan converter, and has functions such as a coordinate conversion function, a pixel interpolation function, and a frame rate conversion function. With respect to each reception beam data array received from the reception unit 16, the image generation unit 18 performs various types of signal processing such as gain correction processing, logarithmic amplification processing, and filter processing. After that, based on a set of frame data composed of a plurality of reception beam data arrays having been subjected to the signal processing, the image generation unit 18 generates a B-mode image in which amplitude (or strength) of reflected waves is represented as brightness. Based on a time series sequence of frame data, the image generation unit 18 generates a time series sequence of ultrasound images (or sequence of B-mode images). The generated B-mode images are transmitted to a display control unit 26 and the processor 46.

A tracking processing unit 20 executes speckle tracking processing of tracking speckles in the time direction based on the time series sequence of B-mode images generated by the image generation unit 18. Since the content of the speckle tracking processing may be the same as that of conventional processing, detailed description thereof will not be given herein. Trajectory information indicating trajectories of the speckles is transmitted to the display control unit 26 and the processor 46.

The elastography processing unit 22 estimates, based on the reception beam data from the reception unit 16, an amount of deformation of the body portion under examination caused in response to a pressure applied by a method such as pressing the probe 12 against the subject's body surface. Since the content of the processing of estimating the amount of deformation may be the same as that of conventional processing, detailed description thereof will not be given herein. In particular, the elastography processing unit 22 estimates a change over time in the amount of deformation of the body portion under examination based on the time series arrays of reception beam data from the reception unit 16. Time series elastography information indicating the estimated change over time in the amount of deformation of the body portion under examination is transmitted to the display control unit 26 and the processor 46.

The Doppler processing unit 24 calculates, based on the reception beam data from the reception unit 16, a velocity of the body portion under examination located within the scan plane or blood flowing in the examined body portion. Since the content of the processing of calculating the velocity of the examined body portion or blood may be the same as that of conventional processing, detailed description thereof will not be given herein. In particular, the Doppler processing unit 24 calculates a change over time in the velocity of the examined body portion located within the scan plane or blood flowing in the examined body portion based on the time series arrays of reception beam data from the reception unit 16. Time series Doppler signals (or time series velocity signals) indicating the calculated change over time in the velocity of the examined body portion or blood are transmitted to the display control unit 26 and the processor 46.

The display control unit 26 causes the B-mode images generated in the image generation unit 18 to be displayed on a display 28, which is a display unit composed of, for example, a liquid crystal panel or the like. In particular, the display control unit 26 causes the time series sequence of B-mode images (that is, a moving image) to be displayed on the display 28. Further, based on the trajectory information from the tracking processing unit 20, the display control unit 26 causes a result of the speckle tracking processing to be displayed on the display 28. Also, based on the time series elastography information from the elastography processing unit 22, the display control unit 26 causes amounts of deformation of the examined body portion to be indicated in color in a superimposed manner over the sequence of B-mode images (or the moving image), so that changes in amount of deformation over time are displayed on the display 28. Additionally, based on the time series Doppler signals from the Doppler processing unit 24, the display control unit 26 causes velocities of the examined body portion or blood to be indicated in color in a superimposed manner over the sequence of B-mode images (or the moving image), so that changes in velocity over time are displayed on the display 28. Furthermore, the display control unit 26 causes a result of prediction by a feature prediction unit 48 described later to be displayed on the display 28.

Each of the transmission unit 14, the reception unit 16, the image generation unit 18, the tracking processing unit 20, the elastography processing unit 22, the Doppler processing unit 24, and the display control unit 26 is composed of one or more processors, chips, electric circuits, or the like. Each of these units may be implemented by cooperation of hardware and software.

An input interface 30 is composed of, for example, a button, a trackball, a touchscreen, or the like. The input interface 30 is a device for inputting a user instruction into the ultrasonic diagnosis apparatus 10.

An electrocardiograph 32 is constituted to include a plurality of electrodes to be attached to a subject's body. The electrocardiograph 32 outputs electrocardiac waveform data, which are the subject's heartbeat waveform, to the processor 46.

A memory 34 is constituted to include a HDD (hard disk drive), an SSD (solid-state drive), an eMMC (embedded MultiMedia Card), a ROM (read-only memory), a RAM (random-access memory), or the like. The memory 34 has stored therein an ultrasound time series data processing program for causing operation of respective components of the ultrasonic diagnosis apparatus 10. The ultrasound time series data processing program may alternatively be stored in a computer-readable, non-transient storage medium such as a USB (Universal Serial Bus) memory or a CD-ROM. The ultrasonic diagnosis apparatus or other computers can read out the ultrasound time series data processing program from such a storage medium and execute the program. Further, as shown in FIG. 1, the memory 34 has stored therein an examination type prediction learner 36, a tissue cross section prediction learner 38, a measurement position prediction learner 40, a disease prediction learner 42, and an artifact prediction learner 44. Each of these learners corresponds to a feature prediction learner.

Each of the examination type prediction learner 36, the tissue cross section prediction learner 38, the measurement position prediction learner 40, the disease prediction learner 42, and the artifact prediction learner 44 is composed of a learning model such as, for example: an RNN (recurrent neural network); an LSTM (long short term memory), which is a type of RNN; a CNN (convolutional neural network); or a DQN (Deep Q-Network), which uses a deep reinforcement learning algorithm. The above-noted learners may all be learning models of the same type, or may be learning models of mutually different types.

Each of the learners is trained using, as training data, a combination of a training set of time series data, which is a set of time series data indicating a change in signal over time and which is generated by repeatedly performing a plurality of times of ultrasound transmission and reception with respect to a single scan plane designated within a subject's body, and information (or a label) indicating a feature regarding the training set of time series data, and each learner is trained to predict and output, based on an input set of time series data, a feature regarding that set of time series data. Specifically, a training set of time series data is input into each learner, and the learner predicts and outputs a feature indicated by that training set of time series data. A computer that carries out a training processing calculates, using a predetermined loss function, an error between the output data and the label assigned to the training set of time series data, and adjusts parameters (e.g., weights or biases of respective neurons) of the learner such that the error becomes reduced. By repeating such training processing, each of the learners is enabled to output, based on an input set of time series data, a feature regarding that set of time series data with high accuracy.

Although the training set of time series data in the present embodiment is a time series sequence of ultrasound images generated by the image generation unit 18, the training set of time series data may alternatively be a time series sequence of frame data, which is data before imaging. Further, in the disease prediction learner 42, the training set of time series data may be trajectory information generated by the tracking processing unit 20, time series elastography information generated by the elastography processing unit 22, or time series Doppler signals generated by the Doppler processing unit 24.

There are cases where a body portion under examination which serves as the subject of the training set of time series data is a pulsating portion. In such cases, the training set of time series data may be a set of data corresponding to a predetermined period within a pulsation cycle of the body portion under examination. For example, it may be to obtain an electrocardiac waveform of a subject from the electrocardiograph 32, and use, as the training set of time series data, a set of time series data based on reception beam data arrays obtained within a period between two R waves in the electrocardiac waveform.

The above-noted "feature" is at least one of: a type of examination to be performed using the set of time series data; a type of tissue cross section shown by the set of time series data; a measurement position that should be designated in ultrasound images corresponding to the set of time series data; a disease indicated by the set of time series data; or a type of artifact generated in the set of time series data. In the present embodiment, a separate learner is provided for each of the features, as described below.

The examination type prediction learner 36 is a learner trained using, as the training data, a combination of the training set of time series data and information indicating a type of examination to be performed using the training set of time series data, so as to predict and output, based on an input set of time series data, a type of examination to be performed using that set of time series data.

The tissue cross section prediction learner 38 is a learner trained using, as the training data, a combination of the training set of time series data and information indicating a tissue cross section (such as, for example, a four-chamber view or a two-chamber view of the heart) shown by ultrasound images (or B-mode images) corresponding to the training set of time series data, so as to predict and output, based on an input set of time series data, a tissue cross section shown by ultrasound images corresponding to that set of time series data.

The measurement position prediction learner 40 is a learner trained using, as the training data, a combination of the training set of time series data and information indicating a measurement position (such as, for example, a position of a tissue or a cursor position in Doppler examination) that should be designated in performing a measurement using the training set of time series data, so as to predict and output, based on an input set of time series data, a measurement position that should be designated in performing a measurement using that set of time series data.

The disease prediction learner 42 is a learner trained using, as the training data, a combination of the training set of time series data and information indicating a disease indicated by the training set of time series data, so as to predict and output, based on an input set of time series data, a disease indicated by that set of time series data.

The artifact prediction learner 44 is a learner trained using, as the training data, a combination of the training set of time series data and information indicating a type of artifact generated in ultrasound images corresponding to the training set of time series data, so as to predict and output, based on an input set of time series data, a type of artifact generated in ultrasound images corresponding to that set of time series data.

In the present embodiment, each of the above-noted learners is trained by a computer other than the ultrasonic diagnosis apparatus 10, and the trained learners are stored in the memory 34. However, the training processing for the learners may alternatively be carried out in the ultrasonic diagnosis apparatus 10 using, as the training set of time series data, a set of time series data obtained by the ultrasonic diagnosis apparatus 10. In that case, the processor 46 performs functions as a training processing unit that carries out the training processing for the learners.

The processor 46 is constituted to include at least one of a general-purpose processing device (such as, for example, a CPU (central processing unit)) or a dedicated processing device (such as, for example, a GPU (graphics processing unit), an ASIC (application-specific integrated circuit), an FPGA (field-programmable gate array), or a programmable logic device. Instead of being composed of a single processing device, the processor 46 may be constituted by cooperation of a plurality of processing devices located at physically separate sites. As shown in FIG. 1, the processor 46 performs functions as a feature prediction unit 48 according to the ultrasound time series data processing program stored in the memory 34.

The feature prediction unit 48 inputs, into each of the above-described trained learners, a set of time series data (referred to as a "target set of time series data" in the present specification) generated by repeatedly performing a plurality of cycles of ultrasound transmission and reception with respect to a single scan plane designated within a subject's body (referred to as a "target subject's body" in the present specification) serving as the target of feature prediction. Although the target set of time series data in the present embodiment is a time series sequence of ultrasound images generated by the image generation unit 18, the target set of time series data may alternatively be a time series sequence of frame data which is data before imaging. Further, in the disease prediction learner 42, the target set of time series data may be trajectory information generated by the tracking processing unit 20, time series elastography information generated by the elastography processing unit 22, or time series Doppler signals generated by the Doppler processing unit 24.

When the target set of time series data is a sequence of ultrasound images, the reception unit 16 and the image generation unit 18 correspond to a time series data generation unit. When the target set of time series data is a time series sequence of frame data which is data before imaging, the reception unit 16 corresponds to the time series data generation unit. When the target set of time series data is trajectory information, the reception unit 16, the image generation unit 18, and the tracking processing unit 20 correspond to the time series data generation unit. When the target set of time series data is time series elastography information, the reception unit 16 and the elastography processing unit 22 correspond to the time series data generation unit. When the target set of time series data is time series Doppler signals, the reception unit 16 and the Doppler processing unit 24 correspond to the time series data generation unit.

Time series data (i.e., a sequence of frame data, a sequence of ultrasound images, trajectory information, time series elastography information, or a set of time series Doppler signals) obtained in the past is temporarily retained in a cine memory (not shown in drawing) for a predetermined period of time. For example, based on an electrocardiac waveform of a target subject obtained using an electrocardiograph 32, time series data corresponding to a plurality of heartbeats are retained. As will be described in detail later, the feature prediction unit 48 selects a target set of time series data from among the retained time series data.

Based on an input target set of time series data, each learner predicts a feature regarding the target set of time series data, and outputs an output data indicating a result of prediction. Based on output data from each learner, the feature prediction unit 48 predicts a feature regarding the target set of time series data.

Specifically, the feature prediction unit 48 inputs a target set of time series data into the trained examination type prediction learner 36, and thereby predicts a type of examination to be performed using the target set of time series data. By inputting a target set of time series data into the trained tissue cross section prediction learner 38, the feature prediction unit 48 predicts a tissue cross section shown by ultrasound images corresponding to the target set of time series data. By inputting a target set of time series data into the trained measurement position prediction learner 40, the feature prediction unit 48 predicts a measurement position that should be designated in performing a measurement using the target set of time series data. A prediction of a type of examination to be performed using the target set of time series data, a prediction of a tissue cross section shown by ultrasound images corresponding to the target set of time series data, or a prediction of a measurement position that should be designated can be helpful to a person not very familiar with diagnosis using ultrasound images. Further, a prediction of a tissue cross section can also be of assistance in performing an automatic processing. For example, when performing processing of automatically tracing a contour of a heart shown in B-mode images, it is necessary for the ultrasonic diagnosis apparatus 10 to recognize in advance that the heart is shown in the B-mode images. The ultrasonic diagnosis apparatus 10 first determines that the heart is shown in the B-mode images by performing a prediction of a tissue cross section, and then can proceed with the processing of automatically tracing the contour of the heart.

Further, the feature prediction unit 48 inputs a target set of time series data into the trained disease prediction learner 42, and thereby predicts a disease indicated by the target set of time series data. As described above, the feature prediction unit 48 can input, into the disease prediction learner 42 as the target set of time series data, trajectory information generated by the tracking processing unit 20, time series elastography information generated by the elastography processing unit 22, or time series Doppler signals generated by the Doppler processing unit 24. When trained using trajectory information as the training data, the disease prediction learner 42 predicts a disease indicated by the target set of time series data based on speckle trajectories. When trained using time series elastography information as the training data, the disease prediction learner 42 predicts a disease indicated by the target set of time series data based on a change over time in amount of deformation of the body portion under examination. When trained using time series Doppler signals as the training data, the disease prediction learner 42 predicts a disease indicated by the target set of time series data based on a change over time in movement velocity of a tissue (e.g., a change in blood flow over time) inside the subject's body.

Further, the feature prediction unit 48 inputs a target set of time series data into the trained artifact prediction learner 44, and thereby predicts a type of artifact generated in ultrasound images corresponding to the target set of time series data. A prediction of a type of artifact generated in ultrasound images corresponding to the target set of time series data can be helpful to a person not very familiar with identifying artifacts generated in ultrasound images.

In the present embodiment, since a plurality of learners trained to predict and output features different from each other are stored in the memory 34, the feature prediction unit 48 inputs a target set of time series data into a learner selected from among the plurality of learners based on a user instruction. A user can directly designate, using the input interface 30, a learner into which a target set of time series data is to be input. Alternatively, the feature prediction unit 48 may be configured to select a learner into which a target set of time series data is to be input based on an operation setting of the ultrasonic diagnosis apparatus 10 set by the user using the input interface 30. For example, when the operation mode of the ultrasonic diagnosis apparatus 10 is a color Doppler mode for effecting a color Doppler function, the feature prediction unit 48 inputs a target set of time series data into the measurement position prediction learner 40 which predicts a Doppler cursor position. Further, when the operation mode of the ultrasonic diagnosis apparatus 10 is a speckle tracking mode for performing speckle tracking, the feature prediction unit 48 inputs a target set of time series data (in this case, trajectory information) into the disease prediction learner 42.

The feature prediction unit 48 may alternatively be configured to input a target set of time series data into respective ones of the plurality of learners and predict a feature regarding that target set of time series data based on a combination of outputs from the plurality of learners. For example, based on an output from the examination type prediction learner 36, the feature prediction unit 48 predicts a type of examination to be performed using the target set of time series data, and identifies a plurality of diseases that can be determined from the predicted type of examination. The process of identifying a plurality of diseases based on the predicted type of examination can be performed by a method such as, for example, referring to a table showing correlations between types of examination and diseases that can be determined from the respective types of examination. After that, by inputting the target set of time series data into the trained disease prediction learner 42, the feature prediction unit 48 predicts a disease indicated by the target set of time series data in a manner of selecting from among the identified plurality of diseases. With this arrangement, accuracy of disease prediction is expected to be further improved. In a similar way, based on an output from the tissue cross section prediction learner 38, the feature prediction unit 48 predicts a tissue cross section shown by ultrasound images corresponding to the target set of time series data, and identifies a plurality of diseases that can be determined from the predicted tissue cross section. The process of identifying a plurality of diseases that can be determined from the predicted tissue cross section can similarly be performed by a method such as, for example, referring to a table showing correlations between tissue cross sections and diseases that can be determined from the respective tissue cross sections. After that, by inputting the target set of time series data into the trained disease prediction learner 42, the feature prediction unit 48 predicts a disease indicated by the target set of time series data in a manner of selecting from among the identified plurality of diseases. With this arrangement, accuracy of disease prediction is expected to be further improved.

The feature prediction unit 48 may alternatively be configured to input a target set of time series data into all of the learners and obtain results of prediction of the respective features from all of the learners in parallel.

As described above, in the present embodiment, each of the learners is trained using a training set of time series data. As a result, each learner is enabled to output a feature of a set of time series data in consideration of a change over time in the set of time series data (i.e., a sequence of frame data, a sequence of ultrasound images, trajectory information, time series elastography information, or time series Doppler signals). By inputting a target set of time series data into a learner trained as such, a feature of an ultrasound image can be predicted more accurately, at least as compared to a case where the feature of the ultrasound image is predicted by inputting the ultrasound image into a learner trained using ultrasound images that are still images.

The target set of time series data and the training set of time series data may be sets of time series data that correspond to the same period of a subject's pulsation cycle in an electrocardiac waveform obtained using the electrocardiograph 32. For example, when the training set of time series data is a set of time series data based on reception beam data arrays obtained during a period between two R waves in an electrocardiac waveform, the target set of time series data used in the feature prediction unit 48 may be also a set of time series data based on reception beam data arrays obtained during a period between two R waves in an electrocardiac waveform. By configuring such that the period of the training set of time series data and the period of the target set of time series data are the same period of a pulsation cycle, accuracy of output from each learner can be improved. In other words, accuracy of prediction by the feature prediction unit 48 in predicting a feature indicated by the target set of time series data is further improved.

The display control unit 26 notifies a result of prediction by the feature prediction unit 48 to the user. That is, the display control unit 26 functions as a notification unit. Although a result of prediction by the feature prediction unit 48 is displayed on the display 28 by the display control unit 26 as described below, a result of prediction by the feature prediction unit 48 may additionally or alternatively be notified to the user by means of audio output.

Figure 3:
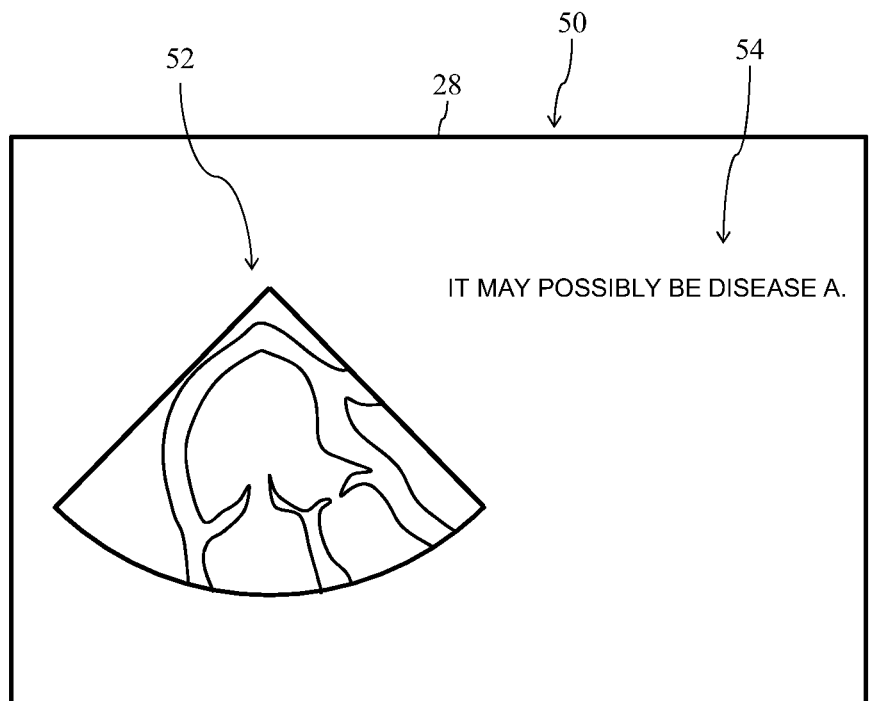
FIG. 3 is a diagram showing an example notification screen notifying a result of prediction by a feature prediction unit.

FIG. 3 is a diagram showing an example notification screen 50 notifying a result of prediction by the feature prediction unit 48. In the notification screen 50, there are displayed ultrasound images 52 (or a moving image) generated based on a target set of time series data, and a result of prediction 54 by the feature prediction unit 48. The notification screen 50 shows a result of prediction of a disease indicated by the target set of time series data, which is predicted by the feature prediction unit 48 using the disease prediction learner 42.

A description will now be given regarding points of time at which the feature prediction unit 48 performs the above-described prediction processing, and regarding methods of selecting a target set of time series data which serves as the object of the prediction processing.

First, the feature prediction unit 48 can execute the prediction processing at a point of time at which an instruction is received from a user. For example, in response to a user inputting a prediction instruction into the ultrasonic diagnosis apparatus 10 using the input interface 30, the feature prediction unit 48 inputs, into a learner, a target set of time series data which has been obtained up to that point, and thereby predicts a feature of the target set of time series data.

Figure 4:
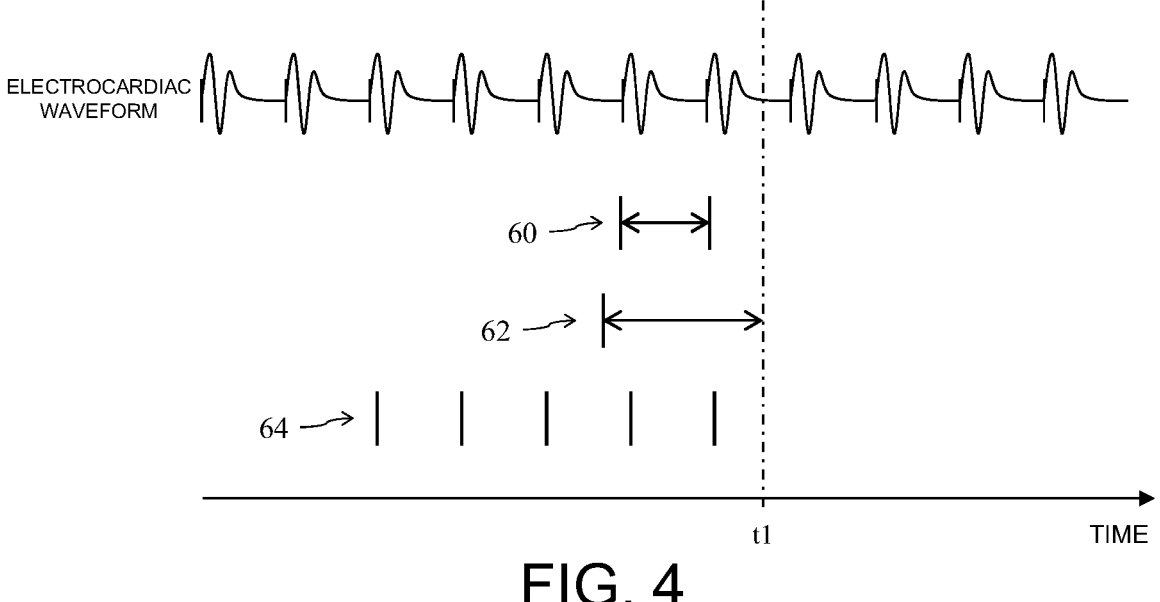
FIG. 4 is a first conceptual diagram showing a point of time at which prediction processing is performed by the feature prediction unit, and also showing target sets of time series data.

FIG. 4 is a diagram showing target sets of time series data for use in a case where the prediction processing is executed at a point of time at which an instruction is received from a user. In FIG. 4 (and also in FIGS. 5 and 6 referred to later), the horizontal axis is the time axis, and a target subject's electrocardiac waveform obtained by the electrocardiograph 32 is shown.

In the example shown in FIG. 4, a user inputs a prediction instruction into the ultrasonic diagnosis apparatus 10 at a time t1, and the feature prediction unit 48 executes the prediction processing at the time t1. In this case, the feature prediction unit 48 selects a target set of time series data from among retained time series data by referring to the time t1 as a reference point.

For example, as shown at reference sign 60 in FIG. 4, the feature prediction unit 48 can use, as the target set of time series data, a set of time series data obtained during one heartbeat period immediately before the time t1 serving as the reference point, which is the time of execution of the prediction processing. Here, a set of time series data corresponding to a period between two R waves in the electrocardiac waveform is used as the target set of time series data. Further, as shown at reference sign 62 in FIG. 4, the feature prediction unit 48 may use, as the target set of time series data, a set of time series data obtained during a predetermined period immediately before the time t1 serving as the reference point. Furthermore, as shown at reference sign 64 in FIG. 4, the feature prediction unit 48 may use, as the target set of time series data, a predetermined number of data items obtained at time points of R waves in the electrocardiac waveform by referring to the time t1 as the reference point. As in the example shown at reference sign 64, a plurality of data items included in the target set of time series data may be temporally discontinuous.

Further, the feature prediction unit 48 may repeatedly execute the prediction processing at predetermined time intervals without depending on any prediction instruction from the user. In this case, the feature prediction unit 48 repeatedly executes prediction of a feature regarding a target set of time series data (e.g., the target set of time series data denoted by reference sign 60, 62, or 64) obtained by referring, as a reference point, to the time of execution of the prediction processing (that is, the current point of time). According to this arrangement, the user can obtain a result of prediction of a feature regarding the most recent target set of time series data.

Figure 5:
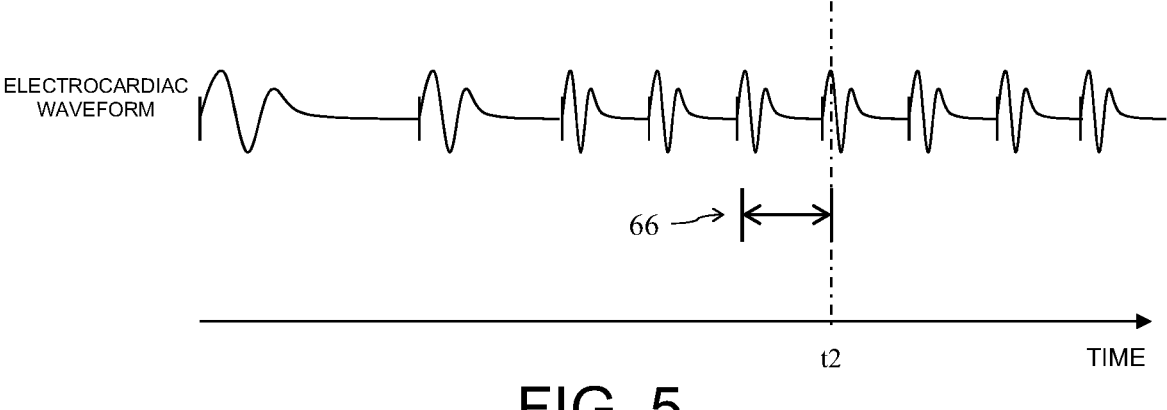
FIG. 5 is a second conceptual diagram showing a point of time at which prediction processing is performed by the feature prediction unit, and also showing a target set of time series data.

Further, the feature prediction unit 48 may execute the prediction processing based on a target subject's electrocardiac waveform obtained by the electrocardiograph 32. Specifically, as shown in FIG. 5, the feature prediction unit 48 may execute the prediction processing at a point of time at which a target subject's heartbeat intervals have become stable. The target subject's heartbeat intervals can be determined, for example, by detecting R waves in the electrocardiac waveform and measuring lengths of time between two R waves. In the example shown in FIG. 5, the prediction processing is executed at a time t2, which is a point at which the heartbeat intervals have been stable for three heartbeats. In this case, the feature prediction unit 48 executes prediction of a feature regarding a target set of time series data obtained by referring, as a reference point, to the time of execution of the prediction processing (i.e., the time t2 in the example of FIG. 5) (here, the target set of time series data is, for example, a set of time series data (reference sign 66 in FIG. 5) obtained during one heartbeat period immediately before the time t2, a set of time series data obtained during a predetermined period immediately before the time t2, a predetermined number of data items obtained at time points of R waves in the electrocardiac waveform by referring to the time t2 as the reference point, or the like). According to this arrangement, it is possible to perform prediction of a feature in a target set of time series data obtained in a state in which the heartbeat intervals are stable.

Further, the feature prediction unit 48 may execute the prediction processing at a point of time determined by reference to a point at which the user has operated the probe 12. Specifically, the feature prediction unit 48 may execute the prediction processing at a point of time at which, subsequent to a change in the attitude of the probe 12, the attitude of the probe 12 has been stable for a predetermined period of time. The feature prediction unit 48 can, for example, determine the attitude of the probe 12 based on a detection signal from an acceleration sensor provided in the probe 12. Further, the feature prediction unit 48 can determine a change in the attitude of the probe 12 based on image changes in B-mode images generated by the image generation unit 18. According to this arrangement, the user can obtain a prediction of a feature regarding a target set of time series data each time the user operates the probe 12. In particular, the user can obtain a prediction of a feature regarding a target set of time series data each time the user changes the attitude of the probe 12.

Figure 6:
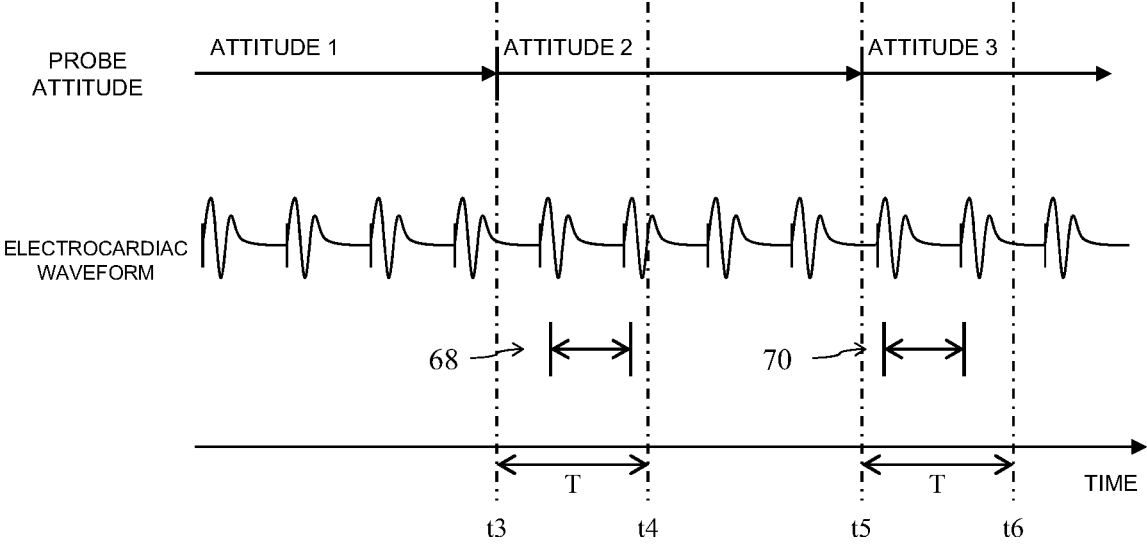
FIG. 6 is a third conceptual diagram showing points of time at which prediction processing is performed by the feature prediction unit, and also showing target sets of time series data.

For example, it is assumed that, as shown in FIG. 6, the user changes the attitude of the probe 12 from an attitude 1 to an attitude 2 at a time t3, and subsequently maintains the probe 12 in the attitude 2. When the feature prediction unit 48 determines that the attitude of the probe 12 has been stable (i.e., that the amount of change in the attitude is maintained at or below a predetermined amount) during a predetermined period T from the time t3 at which the change in the attitude of the probe 12 was detected, the feature prediction unit 48 executes the prediction processing at a time t4, which is the point of time after elapse of the predetermined period T from the time t3. In this case, the feature prediction unit 48 executes prediction of a feature regarding a target set of time series data obtained by referring, as a reference point, to the time of execution of the prediction processing (i.e., the time t4 in the example of FIG. 6) (here, the target set of time series data is, for example, a set of time series data (reference sign 68 in FIG. 6) obtained during one heartbeat period immediately before the time t4, a set of time series data obtained during a predetermined period immediately before t4, a predetermined number of data items obtained at time points of R waves in the electrocardiac waveform by referring to the time t4 as the reference point, or the like).

It is further assumed that, in a manner similar to the above, the user changes the attitude of the probe 12 from the attitude 2 to an attitude 3 at a time t5, and subsequently maintains the probe 12 in the attitude 3. When the feature prediction unit 48 determines that the attitude of the probe 12 has been stable during a predetermined period T from the time t5 at which the change in the attitude of the probe 12 was detected, the feature prediction unit 48 executes the prediction processing at a time t6, which is the point of time after elapse of the predetermined period T from the time t5. In this case, the feature prediction unit 48 executes prediction of a feature regarding a target set of time series data obtained by referring, as a reference point, to the time of execution of the prediction processing (i.e., the time t6 in the example of FIG. 6) (here, the target set of time series data is, for example, a set of time series data (reference sign 70 in FIG. 6) obtained during one heartbeat period immediately before the time t6, a set of time series data obtained during a predetermined period immediately before t6, a predetermined number of data items obtained at time points of R waves in the electrocardiac waveform by referring to the time t6 as the reference point, or the like).

Figure 7:
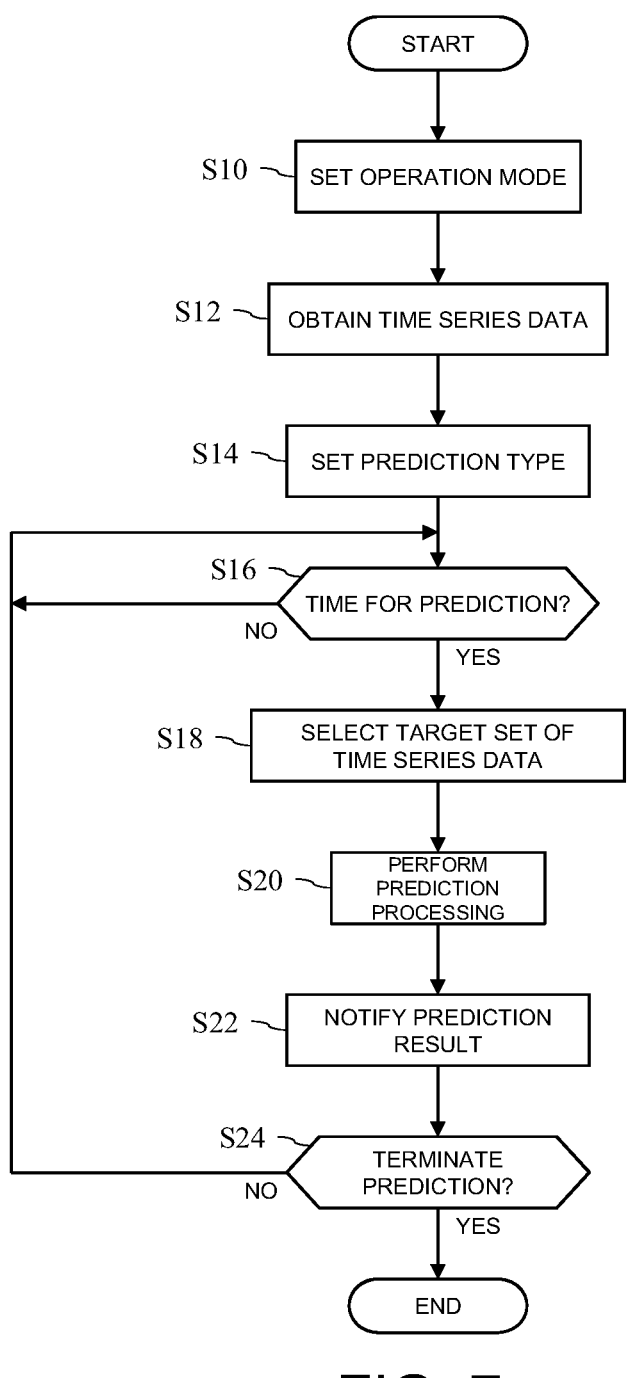
FIG. 7 is a flowchart showing a flow of processing performed by the ultrasonic diagnosis apparatus according to the embodiment.

A flow of processing performed by the ultrasonic diagnosis apparatus 10 according to the present embodiment will now be described by reference to the flowchart shown in FIG. 7.

In step S10, the ultrasonic diagnosis apparatus 10 sets the operation mode according to a user instruction from the input interface 30. The operation mode is, for example, a B mode for generating B-mode images, a speckle tracking mode for performing speckle tracking, an elastography mode for effecting the elastography function, a color Doppler mode for effecting a color Doppler function, or the like.

In step S12, ultrasound transmission and reception are performed by the probe 12 with respect to a target subject's body, and as a result, time series data (i.e., a sequence of frame data, a sequence of ultrasound images, trajectory information, time series elastography information, or a set of time series Doppler signals) are obtained. The time series data are retained in the cine memory or the like.

In step S14, the feature prediction unit 48 sets a type of feature to be predicted regarding a target set of time series data. In other words, the feature prediction unit 48 selects, from among the plurality of learners stored in the memory 34, a learner into which a target set of time series data is to be input. The feature prediction unit 48 may select the learner based on an instruction input into the input interface 30 by the user, or may select the learner based on the operation mode of the ultrasonic diagnosis apparatus 10 set in step S10.

In step S16, the feature prediction unit 48 determines whether or not a point of time for executing the prediction processing is reached. As described above, a point of time for executing the prediction processing is: a point at which an instruction is received from the user; in a case where the prediction processing is to be performed at predetermined time intervals, a point at which at predetermined period of time has elapsed from the previous execution of prediction; a point at which the target subject's heartbeat intervals have become stable; a point at which, subsequent to a change in the attitude of the probe 12, the attitude of the probe 12 has been stable for a predetermined period of time; or the like. The feature prediction unit 48 waits until a point of time for executing the prediction processing is reached, and proceeds to step S18 when a point of time for executing the prediction processing is reached.

In step S18, the feature prediction unit 48 selects, from among the time series data retained in step S12, a target set of time series data by referring to the time of execution of the prediction processing as a reference point. For example, the feature prediction unit 48 selects, as the target set of time series data: a set of time series data obtained during one heartbeat period immediately before the time of execution of the prediction processing; a set of time series data obtained during a predetermined period immediately before the time of execution of the prediction processing; a predetermined number of data items obtained at time points of R waves in an electrocardiac waveform by referring to the time of execution of the prediction processing as the reference point; or the like.

In step S20, the feature prediction unit 48 inputs the target set of time series data selected in step S18 into the learner selected in step S14. The feature prediction unit 48 then predicts the feature regarding the target set of time series data based on output data from the learner.

In step S22, the display control unit 26 notifies a result of prediction by the feature prediction unit 48 to the user (see FIG. 3).

In step S24, the processor 46 determines whether or not a termination instruction to terminate the prediction processing is input by the user. When no termination instruction is input, the process returns to step S16, and the processing from step S16 to step S24 is repeated. When the termination instruction is input, the processing ends.

Although an ultrasound time series data processing apparatus according to the present disclosure has been described above, an ultrasound time series data processing apparatus according to the present disclosure is not limited to the above-described embodiment. Various changes are possible so long as those changes do not depart from the scope of the present disclosure.

For example, although the ultrasound time series data processing apparatus in the above-described embodiment is an ultrasonic diagnosis apparatus 10, an ultrasound time series data processing apparatus is not limited to an ultrasonic diagnosis apparatus 10, and may be in the form of other computers. In that case, the trained learners are stored in a memory accessible by a computer serving as the ultrasound time series data processing apparatus, and a processor of the computer performs functions as the feature prediction unit 48 and the display control unit 26.

The invention claimed is:

1. An ultrasound time series data processing apparatus, comprising:

a non-transitory storage medium tangibly embodying one or more programs of instructions; and one or more processors configured to execute the one or more programs of instructions embodied in the non-transitory storage medium to input, into a feature prediction learner, a target set of time series data which is a set of time series data generated by repeatedly performing a plurality of cycles of ultrasound transmission and reception with respect to a single scan plane designated within a target subject's body, each item of data in the target set of time series data representing a cross section of the target subject's body along the scan plane, and to predict a feature regarding the target set of time series data based on an output from the feature prediction learner in response to said input, the feature prediction learner having been trained using, as training data, a combination of a training set of time series data and information indicating a feature regarding the training set of time series data, the training set of time series data being a set of time series data indicating a change in signal over time and being generated by repeatedly performing a plurality of cycles of ultrasound transmission and reception with respect to a single scan plane designated within a subject's body, each item of data in the training set of time series data representing a cross section of the target subject's body along the scan plane, and the feature prediction learner having been trained to predict and output, based on an input set of time series data, a feature regarding that set of time series data; and the one or more processors executing the one or more programs of instructions being further configured to notify a result of the prediction to a user.

2. The ultrasound time series data processing apparatus according to claim 1, wherein the feature is at least one of: a type of examination to be performed using a set of time series data; a type of tissue cross section shown by the set of time series data; a measurement position that should be designated; a disease indicated by the set of time series data; or a type of artifact generated in the set of time series data.

3. The ultrasound time series data processing apparatus according to claim 1, wherein the set of time series data is at least one of: a time series sequence of ultrasound images;

a time series sequence of frame data, which is data before imaging; trajectory information showing a trajectory of a speckle; time series elastography information indicating a change in amount of deformation over time of a body portion under examination; and time series Doppler signals indicating a change in velocity over time of a body portion under examination or blood.

4. The ultrasound time series data processing apparatus according to claim 1, wherein the one or more processors are further configured to input the target set of time series data into the feature prediction learner which is selected based on a user instruction from among a plurality of feature prediction learners trained to predict and output features different from each other.

5. An ultrasound time series data processing apparatus, comprising:

a non-transitory storage medium tangibly embodying one or more programs of instructions; and one or more processors configured to execute the one or more programs of instructions embodied in the non-transitory storage medium to input, into a feature prediction learner, a target set of time series data which is a set of time series data generated by repeatedly performing a plurality of cycles of ultrasound transmission and reception with respect to a single scan plane designated within a target subject's body, each item of data in the target set of time series data representing a cross section of the target subject's body along the scan plane, and to predict a feature regarding the target set of time series data based on an output from the feature prediction learner in response to said input, wherein the feature prediction learner is trained using, as training data, a combination of a training set of time series data and information indicating a feature regarding the training set of time series data, the training set of time series data being a set of time series data indicating a change in signal over time and being generated by repeatedly performing a plurality of cycles of ultrasound transmission and reception with respect to a single scan plane designated within a subject's body, each item of data in the training set of time series data representing a cross section of the target subject's body along the scan plane, and wherein the feature prediction learner is trained to predict and output, based on an input set of time series data, a feature regarding that set of time series data, wherein the one or more processors are further configured to notify a result of the prediction to a user, and to input the target set of time series data into a plurality of feature prediction learners each of which is said feature prediction learner and which are trained to predict and output features different from each other, and to predict the feature regarding the target set of time series data based on a combination of outputs from the plurality of feature prediction learners.

6. The ultrasound time series data processing apparatus according to claim 1, wherein the target set of time series data and the training set of time series data are sets of time series data that correspond to the same period of a pulsation cycle of a subject.

7. The ultrasound time series data processing apparatus according to claim 1, wherein the one or more processors are further configured to generate the target set of time series data.

8. The ultrasound time series data processing apparatus according to claim 7, wherein the one or more processors are further configured to repeatedly execute prediction of the feature regarding the target set of time series data obtained by referring to a current point of time as a reference point.

9. The ultrasound time series data processing apparatus according to claim 7, wherein the one or more processors are further configured to execute, based on an electrocardiac waveform obtained from the target subject, prediction of the feature regarding the target set of time series data obtained by referring, as a reference point, to a point of time at which the target subject's heartbeat intervals have become stable.

10. The ultrasound time series data processing apparatus according to claim 7, wherein the one or more processors are further configured to execute prediction of the feature regarding the target set of time series data obtained by referring, as a reference point, to a point of time at which a user has operated an ultrasound probe configured to perform ultrasound transmission and reception.

11. A computer-readable non-transient storage medium having stored therein instructions executable by a computer, wherein the instructions are configured to cause a computer to execute:

a feature prediction step of inputting, into a feature prediction learner, a target set of time series data which is a set of time series data generated by repeatedly performing a plurality of cycles of ultrasound transmission and reception with respect to a single scan plane designated within a target subject's body, each item of data in the target set of time series data representing a cross section of the target subject's body along the scan plane, and predicting a feature regarding the target set of time series data based on an output from the feature prediction learner in response to said input, the feature prediction learner having been trained using, as training data, a combination of a training set of time series data and information indicating a feature regarding the training set of time series data, the training set of time series data being a set of time series data indicating a change in signal over time and being generated by repeatedly performing a plurality of times of ultrasound transmission and reception with respect to a single scan plane designated within a subject's body, each item of data in the training set of time series data representing a cross section of the target subject's body along the scan plane, and the feature prediction learner having been trained to predict and output, based on an input set of time series data, a feature regarding that set of time series data; and a notification step of notifying a result of the prediction to a user.

12. The computer-readable non-transient storage medium according to claim 11, wherein the instructions are further configured to cause the computer to input the target set of time series data into the feature prediction learner which is selected based on a user instruction from among a plurality of feature prediction learners trained to predict and output features different from each other.

13. The computer-readable non-transient storage medium according to claim 11, wherein the target set of time series data and the training set of time series data are sets of time series data that correspond to the same period of a pulsation cycle of a subject.

14. The computer-readable non-transient storage medium according to claim 11, wherein the instructions are further configured to cause the computer to repeatedly execute prediction of the feature regarding the target set of time series data obtained by referring to a current point of time as a reference point.

15. The computer-readable non-transient storage medium according to claim 11, wherein the instructions are further configured to cause the computer to execute, based on an electrocardiac waveform obtained from the target subject, prediction of the feature regarding the target set of time series data obtained by referring, as a reference point, to a point of time at which the target subject's heartbeat intervals have become stable.

\* \* \* \* \*